United States Patent
Barry

(10) Patent No.: US 11,065,290 B2
(45) Date of Patent: *Jul. 20, 2021

(54) TOPICAL COMPOSITION

(71) Applicant: BIOPHARM NZ LIMITED, Hamilton (NZ)

(72) Inventor: Michael-John Joseph Barry, Hamilton (NZ)

(73) Assignee: BIOPHARM NZ LIMITED, Hamilton (NZ)

(*) Notice: Subject to any disclaimer, the term of this patent is extended or adjusted under 35 U.S.C. 154(b) by 141 days.

This patent is subject to a terminal disclaimer.

(21) Appl. No.: 16/083,802

(22) PCT Filed: Mar. 9, 2017

(86) PCT No.: PCT/IB2017/051388
§ 371 (c)(1),
(2) Date: Sep. 10, 2018

(87) PCT Pub. No.: WO2017/153943
PCT Pub. Date: Sep. 14, 2017

(65) Prior Publication Data
US 2019/0083562 A1  Mar. 21, 2019

(30) Foreign Application Priority Data
Mar. 9, 2016 (ZA) .................. 2016/00677

(51) Int. Cl.
| A61K 36/185 | (2006.01) |
| A61K 36/48 | (2006.01) |
| A61K 9/00 | (2006.01) |
| A61K 36/36 | (2006.01) |
| A61Q 19/00 | (2006.01) |
| A61K 9/06 | (2006.01) |
| A61K 8/9789 | (2017.01) |
| A61P 17/10 | (2006.01) |
| A61P 17/06 | (2006.01) |
| A61P 17/02 | (2006.01) |
| A61P 31/04 | (2006.01) |
| A61P 31/10 | (2006.01) |
| A61K 8/34 | (2006.01) |
| A61K 8/365 | (2006.01) |
| A61K 8/46 | (2006.01) |
| A61K 8/67 | (2006.01) |
| A61K 8/73 | (2006.01) |
| A61K 47/10 | (2017.01) |
| A61K 47/12 | (2006.01) |
| A61K 47/18 | (2017.01) |
| A61K 47/20 | (2006.01) |
| A61K 47/46 | (2006.01) |
| A61Q 5/02 | (2006.01) |
| A61Q 19/10 | (2006.01) |

(52) U.S. Cl.
CPC .............. *A61K 36/48* (2013.01); *A61K 8/345* (2013.01); *A61K 8/365* (2013.01); *A61K 8/466* (2013.01); *A61K 8/673* (2013.01); *A61K 8/73* (2013.01); *A61K 8/9789* (2017.08); *A61K 9/0014* (2013.01); *A61K 9/06* (2013.01); *A61K 36/36* (2013.01); *A61K 47/10* (2013.01); *A61K 47/12* (2013.01); *A61K 47/18* (2013.01); *A61K 47/20* (2013.01); *A61K 47/46* (2013.01); *A61P 17/02* (2018.01); *A61P 17/06* (2018.01); *A61P 17/10* (2018.01); *A61P 31/04* (2018.01); *A61P 31/10* (2018.01); *A61Q 5/02* (2013.01); *A61Q 19/00* (2013.01); *A61Q 19/10* (2013.01); *A61K 2800/524* (2013.01); *A61K 2800/5922* (2013.01)

(58) Field of Classification Search
CPC ................................... A61K 36/185
See application file for complete search history.

(56) References Cited

U.S. PATENT DOCUMENTS

| 2010/0119463 A1 | 5/2010 | Jacobs | |
| 2015/0335033 A1* | 11/2015 | Klaasen | ................... A01H 3/04 504/117 |

FOREIGN PATENT DOCUMENTS

ZA  200906942  2/2012

OTHER PUBLICATIONS

International Search Report dated Apr. 13, 2017 from corresponding International Application No. PCT/IB2017/051388.
Vries, et al, "An antifungal active extract from the aerial parts of *Galenia africana*", retrieved from the internet Apr. 3, 2017, pp. 123-131, 11th NAPRECA Symposium Book of Proceedings, Antananarivo, Madagascar (2005).
Omoregie, E.S. et al, "In Vitro Antioxidant Activity and the Effect of Methanolic Extracts of Some Local Plants on Nutritionally Stressed Rats", 2011, pp. 23-56, vol. 1, Pharmacologyonline.
Mativandlela, S.P.N., et al, "Activity against *Mycobacterium smegmatis* and *M. tuberculosis* by Extract of South African medicinal plants", 2008, pp. 841-845, vol. 22, issue 6, Phytotherapy Research.

* cited by examiner

*Primary Examiner* — Rosanne Kosson
(74) *Attorney, Agent, or Firm* — Stephen J. Weyer, Esq.; Stites & Harbison, PLLC

(57) ABSTRACT

The invention discloses a therapeutic topical composition, includes an extract of *Galenia Africana* having anti-microbial and anti-oxidant action. The composition includes rooibos and/or an extract from rooibos tea plant. The composition is adapted for regenerating skin, stimulating cytokeratin production, treating human external fungal infections and/or conditions, human skin bacterial conditions, psoriasis, psoriasis plaque, dandruff, acne, bacterial acnes, eczema, athletes' foot, nappy rash, baby rash and/or lesions and/or being used for anti-septic wound treatment, and/or treating *Propionibacterium acnes* and/or *staphylococcus epidermidis*.

15 Claims, No Drawings

TOPICAL COMPOSITION

FIELD OF INVENTION

The present invention relates to a therapeutic topical composition.

More particularly, the present invention relates to a therapeutic topical composition which includes an extract of *Galenia Africana* and which is adapted to be used for personal care and cosmetic applications.

BACKGROUND TO INVENTION

KBO5 is a plant extract isolated from *Galenia Africana* L. plant containing several bioflavonoids.

It is an object of the invention to suggest a novel therapeutic topical composition which includes an extract of *Galenia Africana*.

SUMMARY OF INVENTION

According to the invention, a therapeutic topical composition includes an extract of *Galenia Africana* having antimicrobial and anti-oxidant action.

Also according to the invention, a method of producing a therapeutic topical composition including an extract of *Galenia Africana* includes the steps
(a) of dissolving KBO5 in a short chain glycol most preferably propylene glycol and/or propanediol to form a liquid concentrate; and
(b) of combining the liquid concentration with different anionic surfactants depending on the end application.

The topical composition may include rooibos and/or an extract from a rooibos tea plant.

The topical composition may be adapted for regenerating skin, stimulating cyto-keratin production, treating human external fungal infections and/or conditions, human skin bacterial conditions, psoriasis, psoriasis plaque, dandruff, acne, bacterial *acnes*, eczema, athletes' foot, nappy rash, baby rash and/or lesions and/or being used for anti-septic wound treatment, and/or treating *Propionibacterium acnes* and/or *staphylococcus epidermidis*.

The topical composition may include leave on or wash off personal care products such as soaps, shampoos, skin moisturiser, toner, salves, creams, balms and/or body wash formulations.

The topical formulation may include active and inactive ingredients in order to improve the activity of KB05.

Different concentrations may be used for different formulations and applications.

The topical composition may include the following compositions and concentrations:

| Ingredients | Formulation A | Formulation B | Formulation C |
|---|---|---|---|
| Deionised water | | 25.5 | |
| Mono propylene glycol | 70.0 | 47 | 60 |
| KBO5 | 30.0 | 20.0 | 20 |
| SAS 93 | | 7.5 | |
| Polysuganate 160 | | | 20.0 |
| Total | 100.00 | 100.0 | 100.0 |

The concentration of KBO5 may be between 0.2 to 5.0%
The desired viscosity may be achieved using polymeric gelling agents.

The topical composition may include the following ingredients and concentrations:

| Formulation D Ingredients | % w/w |
|---|---|
| Deionised water | 40.00 |
| Whole milk | 13.30 |
| Sodium cocoyl glutamate | 10.00 |
| Sodium N lauroylsarcosinate | 10.00 |
| Sodium laurelglucosides hydroxypropyl sulphonate | 10.00 |
| D panthenol | 0.5 |
| Betain | 0.5 |
| Propylene glycol | 4.0 |
| Cocamidopropyl hydroxysultaine | 5.0 |
| Propylene glycol + KBO5 | 5.0 |
| Phenethyl alcohol | 0.5 |
| Citric acid | ±0.2 (to pH 6.5) |
| Xanthan gum | 1.0 |
| Total | 100.0 |

The topical composition may include disodium cocoyl glutamate, sodium lauroyl sarcosinate and/or sulphonated alkyl polyglucoside as very mild anionic surfactants that work together to give a rich creamy foam that helps to reinforce the goats milk creaminess perception.

The topical composition may include cocamidopropyl hydroxysultaine, an amphoteric surfactant that helps to stabilise the foam of the anionic surfactants and adds to surfactant mildness. The Colateric CBS may be replaced by cocoamidopropyl betain which is also naturally derived but is mildly irritating.

The topical composition may include D Panthenol or vitamin B5 as a nutrient that is easily absorbed by hair and skin with conditioning properties.

The topical composition may include natural betain as a natural ingredient from sugar beet that has the ability to penetrate the skin and hair and act as a moisturiser, it has the added advantage of reducing skin irritation.

The topical composition may include a cosmetic grade of xanthan gum which is added to increase the viscosity of the product, improve foaming properties and skin feel.

The topical composition may include citric acid to adjust the pH.

The topical composition may or may not include natural and/or nature identical preservatives such as phenethyl alcohol, sorbic acid, benzoic acid, caprylyl glycol, sorbitan caprylate and blends of these materials.

The topical composition may include whole mammalian milk for its perceived beneficial properties.

The topical composition may include the following ingredients and concentrations:

| Formulation E Ingredients | % w/w |
|---|---|
| Deionised Water | 21.3 |
| Laurel Glucoside | 20.00 |
| Sodium laureth sulphate | 40 |
| Cocoamidopropyl betain | 10.00 |
| D panthenol | 0.5 |
| Betain | 0.5 |
| Sodium chloride | 5.0 |
| Propylene glycol + KBO5 | 2 |
| Phenethyl alcohol | 0.5 |
| Citric acid | ±0.2 (to pH 6.5) |
| Total | 100.0 |

The KBO5 may be incorporated into a toiletry soap made by industrial methods or from handmade soap without removing the glycerine.

The KOB5 concentration may range from 0.1 to 2.0% in this type of toiletry soaps.

The KOB5 concentration may range from 0.1 to 2.0% in this type of industrial scale soaps.

Beeswax or microcrystalline paraffin wax may be used to increase the viscosity of pastes and salves containing natural or synthetic oils such as almond oil and mineral oil respectively.

The topical composition may include the following ingredients and concentrations:

| Wax thickened oil examples (Heavy paste -water resistant) Ingredients | Formulation F | Formulation G |
|---|---|---|
| Beeswax white | 8.0 | |
| Coconut oil | 36.9 | |
| Castor oil | 5.0 | 20.0 |
| Rice bran oil | 45.0 | |
| Vitamin E | 0.1 | |
| Formulation C | 5.0 | 10.0 |
| Coronet Lanolin | — | 70.0 |
| Total | 100 | |

All the ingredients besides Formulation A may be combined and heated to 70° C. to form a clear homogeneous mixture.

The ingredients may be allowed to cool to about 50° C. before blending in Formulation C and hot filled into tins or glass jars producing a product with the consistency of Tiger Balm.

The topical composition may include the following ingredients and concentrations:

| Mineral thickened paste examples (suitable for tube filling) Ingredients | Formulation H (penetrating) | Formulation I (non-penetrating) |
|---|---|---|
| Floraester 15 (Jojoba ester) | 50.0 | — |
| Dimethyl sorbide | 10.0 | — |
| Castor oil | 10.0 | 10.0 |
| Aerosil 200 (fumed silica) | 8.0 | 8.0 |
| Medium chain triglyceride | — | 60.0 |
| Formulation C | 22.0 | 22.0 |

The oils may be mixed together before adding the fumed silica and blended to form a paste after which the Formulation C is blended in.

The formulations H and I are produced cold and can also be cold filled with a piston filler into tubes or tubs, etc.

The topical composition may include the following ingredients and concentrations:

| Pumpable cream formulation example ingredients | % w/w Formulation J |
|---|---|
| Oil phase | |
| Cetyl alcohol | 5.0 |
| Glycerol monostearate | 3.0 |
| Coconut oil | 15.0 |
| Vitamin E | 0.05 |
| Water phase | |
| Deionised water | 55.75 |
| Betaine | 1.0 |
| Xanthan gum | 0.2 |
| Formulation C | 20.0 |
| Total | 100.0 |

DETAILED DESCRIPTION OF INVENTION

The invention will now be described by way of example.

According to the invention, a therapeutic topical composition includes an extract of *Galenia Africana*.

The topical composition is adapted for regenerating skin, stimulating cyto-keratin production, treating human external fungal infections and/or conditions, human skin bacterial conditions, psoriasis, psoriasis plaque, dandruff, acne, bacterial *acnes*, eczema, athletes' foot, nappy rash, baby rash and/or lesions and/or being used for anti-septic wound treatment, and/or treating *Propionibacterium acnes* and/or *staphylococcus epidermidis*.

The topical composition includes personal care products such as soaps, shampoos, skin moisturiser, toner, salves, creams, balms and/or body wash formulations.

The topical formulation includes active and inactive ingredients in order to improve the activity of KB05.

The most important and/or dominant active ingredient is KB05.

The topical composition may include rooibos and/or an extract from rooibos tea plant.

Concentrations

Different concentration are used for different formulations and applications. KBO5 is formulated into a liquid concentrate by dissolving the material in glycol and then is combined with different anionic surfactants depending on the end application. The following list of concentrates serve as examples.

| Ingredients | Formulation A | Formulation B | Formulation C |
|---|---|---|---|
| De ionised water | | 25.5 | |
| Mono propylene glycol | 70.0 | 47 | 60 |
| KBO5 | 30.0 | 20.0 | 20 |
| SAS 93 | | 7.5 | |
| Polysuganate 160 | | | 20.0 |
| Total | 100.00 | 100.0 | 100.0 |

Shampoo and Body Wash Containing KBO5

The formulations include KBO5 at a therapeutic level, however, it is more cost effective to apply a KBO5 containing salve or cream to the affected area where the concentration can be increased and the active ingredient remains in contact with the affected area for a longer period. Wash off products are important to complement the effect. There are many formulations that can be used and the concentrations of KBO5 between 0.2 to 5.0% are relevant to this category of product. An example of a very mild formulation and a more conventional formulation are given.

Very Mild Formulation D

It was found that formulation C had a viscosity reducing effect on the shampoo formulations that rely on a surfactant electrolyte interaction to build viscosity. Formulation C contained a high proportion of glycol which is essential for the solubilisation of KOB5 but it also reduces the thickening effect of anionic surfactants that interact with electrolytes such as sodium chloride to form syrupy gels. In addition the most efficient surfactants that have this effect such as Sodium laurel ether sulphate are also widely regarded by "natural product" purchasers as being "bad chemicals".

Tests showed that the desired viscosity could only be achieved using polymeric gelling agents. Non-ionic surfactants were avoided due to their historical negative impact on phenolic compound biological efficacy.

| Formulation D Ingredients | % w/w |
|---|---|
| Deionised water | 40.00 |
| Goat milk | 13.30 |
| Sodium cocoyl glutamate | 10.00 |
| Sodium N lauroylsarcosinate | 10.00 |
| Sodium laurelglucosides hydroxypropyl sulphonate | 10.00 |
| D panthenol | 0.5 |
| Betain | 0.5 |
| Propylene glycol | 4.0 |
| Cocamidopropyl hydroxysultaine | 5.0 |
| Propylene glycol + KBO5 | 5.0 |
| Phenethyl alcohol | 0.5 |
| Citric acid | ±0.2 (to pH 6.5) |
| Xanthan gum | 1.0 |
| Total | 100.0 |

The ingredients have the following functions:
(a) Plantapon ACG, Crodasinic LS30 and polysuganate 160N are all very mild anionic surfactants that work together to give rich creamy foam that helps to reinforce the goats milk creaminess perception.
(b) Colateric CBS is an amphoteric surfactant that helps to stabilise the foam of the anionic surfactants and adds to surfactant mildness. This can be replaced by cocoamidopropyl betain which is also naturally derived but thought to be mildly irritating.
(c) D Panthenol or vitamin B5 is a nutrient that is easily absorbed by hair and skin with conditioning properties.
(d) Betafin BP 20 is a natural ingredient from sugar beet that has the ability to penetrate the skin and hair and act as a moisturiser, it has the added advantage of reducing skin irritation.
(e) Keltrol CG is a cosmetic grade of xanthan gum which is added to increase the viscosity of the product, improve foaming properties and skin feel. Xanthan gum can give a congealed viscosity and levels will have to be adjusted to achieve desired results. The viscosity is not affected by propylene glycol and other glycols and the material is completely naturally derived.
(f) Citric acid is added to adjust the pH. The ideal pH of personal care products is 5.5. However, milk curdles in acidic environments and so we have aimed at a pH of 6.5, close to neutral.
(g) Phenethyl alcohol is a nature identical material. The natural product is found in roses and is added as a preservative. The natural product is available but is expensive.
(h) Goat Milk is added for its perceived beneficial properties.

Conventional Formulation E

Formulation E is a concentrated shampoo formulation allowing a small container to be used for many applications of the product for example using a pump action dispenser. This formulation can be varied to enable it to be suitable as a shampoo, body wash or hand wash. The KBO5 level can also be varied between 0.5 and 5% as required.

| Formulation E Ingredients | % w/w |
|---|---|
| Deionised Water | 21.3 |
| Laurel Glucoside | 20.00 |
| Sodium laureth sulphate | 40 |
| Cocoamidopropyl betain | 10.00 |
| D panthenol | 0.5 |
| Betain | 0.5 |
| Sodium chloride | 5.0 |
| Propylene glycol + KBO5 | 2 |
| Phenethyl alcohol | 0.5 |
| Citric acid | ±0.2 (to pH 6.5) |
| Total | 100.0 |

This formulation is much simpler to manufacture from readily available raw materials and the surfactants are all produced using naturally derived raw materials in this case.

Toiletry Soap

KBO5 can be incorporated into a toiletry soap made by industrial methods or from handmade soap without removing the glycerine.

Handmade Soap

It is possible to produce soaps by reacting fats or fatty acids with a strong alkali with a minimum amount of water and allowing fats and oils to be saponified. The triglyceride bond is broken, liberating free fatty acids which are neutralised by the alkali to form the salt or soap and glycerine which in industrial processes is removed but in many of the handmade soaps is left in place to act as a moisturiser.

The KOB5 can be added to the soap soon after addition of the alkali in liquid, for example Formulation A or preferably Formulation C where the polysuganate assists with even dispersion of the KOB5 and improves the cleansing properties of the soap bar.

The mixture is then cast into moulds and allowed to be fully neutralised before demoulding and packing.

The KOB5 concentration can range from 0.1 to 2.0% in this type of soap.

Industrial Scale Soap

It is general practice for soaps to be produced on industrial scale either in a batch process or in a continuous process. The principle is the same as for handmade soap but most of the glycerine is removed together with the water that is required for the saponification reaction to take place. In the batch process, fat is heated up together with water and a strong alkali, normally sodium hydroxide. After saponification, salt is added to the water which causes the soap to separate from the glycerine and water and float to the surface. The glycerine containing salty water or brine is drained off leaving behind the soap which is further refined and eventually extruded into noodles.

The noodles are then mixed together with other ingredients such as stabilisers, fragrance and colour and milled to ensure intimate mixing before being extruded and cut and pressed into its final shape.

KOB5 is most conveniently added at the stage when fragrances, etc. are added and then milled, preferably through a triple roll mill, and extruded.

As with handmade soap either Formulation A or Formulation C could be used as the source of KOB5 for this soap. It is also possible to finely grind the KOB5 and add this fine powder at the same stage, but using this method runs the risk of visible dark spots if the grind is not fine enough.

The KOB5 concentration can range from 0.1 to 2.0% in this type of soap.

Creams and Salves

The full benefit of KBO5 is best achieved using leave on products. These can be produced in a number of ways such as wax thickened oils, mineral thickened oils and oil water emulsions.

Wax Thickened Oil

Beeswax or microcrystalline paraffin wax has been used traditionally to increase the viscosity of pastes and salves containing natural or synthetic oils such as almond oil and mineral oil respectively. KBO5, which is not very oil soluble, can be included in these formulations by using a surfactant based mixture such as Formulation A which is preferred because of the mild nature of the surfactant.

| Wax thickened oil examples (Heavy paste -water resistant) Ingredients | Formulation F | Formulation G |
|---|---|---|
| Beeswax white | 8.0 | |
| Coconut oil | 36.9 | |
| Castor oil | 5.0 | 20.0 |
| Rice bran oil | 45.0 | |
| Vitamin E | 0.1 | |
| Formulation C | 5.0 | 10.0 |
| Coronet Lanolin | — | 70.0 |
| Total | 100 | |

All the ingredients besides Formulation A are combined and heated to 70° C. to form a clear homogeneous mixture. The ingredients are allowed to cool to about 50° C. before blending in Formulation C and hot filled into tins or glass jars producing a product with the consistency of Tiger Balm.

Mineral Thickened Oil

It is possible to produce a balm or salve that is cold processed using natural or synthetic oily substances that are mixed with finely divided minerals to increase the viscosity to the desired level. Fumed silica is particularly effective in achieving the desired effect; lower levels of fumed silica can result in a gel-like product that is quite flow-able and higher levels can be used to achieve a more pasty consistency. The oily substances can be chosen to enhance penetration or reduce penetration into the skin. Higher levels of KOB5 can be achieved using this type of formulation. An antioxidant such as vitamin E can be added if required, however, KOB5 is expected to have good antioxidant properties in its own right.

| Mineral thickened paste examples (suitable for tube filling) Ingredients | Formulation H (penetrating) | Formulation I (non-penetrating) |
|---|---|---|
| Floraester 15 (Jojoba ester) | 50.0 | — |
| Dimethyl sorbide | 10.0 | — |
| Castor oil | 10.0 | 10.0 |
| Aerosil 200 (fumed silica) | 8.0 | 8.0 |
| Medium chain triglyceride | — | 60.0 |
| Formulation C | 22.0 | 22.0 |

Oils are mixed together before adding the fumed silica and blended to form a paste after which the Formulation C is blended in.

The formulation is produced cold and can also be cold filled with a piston filler into tubes or tubs etc.

Emulsion Based Creams and Lotions

Most modern creams and lotions are based on non-ionic surfactant emulsifiers. This is not an option for KBO5 as biological efficacy is reduced. Anionic surfactants such as SAS, laurel sulphates and most preferably sulphonated alkyl polyglucosides such as polysuganate used in Formulation C are suitable as emulsifiers. The amount of oil and wax can be adjusted in order to give products of different viscosities. Emollients with penetrating properties such as dimethyl sorbide or isopropyl myristate can be included to enhance absorption of the KBO5.

| Pumpable cream formulation example ingredients | % w/w Formulation J |
|---|---|
| Oil phase | |
| Cetyl alcohol | 5.0 |
| Glycerol monostearate | 3.0 |
| Coconut oil | 15.0 |
| Vitamin E | 0.05 |
| Water phase | |
| Deionised water | 55.75 |
| Betaine | 1.0 |
| Xanthan gum | 0.2 |
| Formulation C | 20.0 |
| Total | 100.0 |

A typical manufacturing procedure is as follows:
 (a) Oil phase is heated to 70° C. separately and mixed until completely dissolved;
 (b) Water phase ingredients blended together and heated to 70° C.;
 (c) Water phase added to oil phase slowly under high shear; and
 (d) The products are stirred slowly until cool and then packed into suitable containers.

CONCLUSION

There are many potential applications for the KBO5 containing concentrates. As can be seen from the examples given, the concentrates allow the inclusion of KBO5 in a convenient manner and the concentrates remain stable on shelf until required for formulating.

The invention claimed is:

1. A therapeutic topical composition, comprising a therapeutically effective amount of an extract of *Galenia africana*, wherein the extract has anti-microbial and anti-oxidant activity, and wherein the composition further comprises a therapeutically effective amount of rooibos and/or an extract from rooibos tea plant.

2. The composition of claim 1, wherein the composition is a leave-on or wash-off personal care product, and wherein the composition is a soap, shampoo, skin moisturiser, toner, salve, cream, balm or body wash.

3. The composition of claim 1, further comprising mono propylene glycol, wherein the composition comprises about 70% mono propylene glycol and about 30% of the *Galena africana* extract.

4. The composition as claimed in claim 1, further comprising deionized water, in an amount of 25.5%, monopropylene glycol, in an amount of 47%, and Sodium C14-17 Sec Alkyl Sulfonate (SAS93), in an amount of 7.7%, wherein the *G. africana* extract is the KB05 extract, wherein the KB05 extract is in an amount of 20%, and wherein the *G. africana* extract comprises bioflavonoids.

5. The composition as claimed in claim 1, further comprising monopropylene glycol, in an amount of 60%, and polysuganate 160, in an amount of 20%, wherein the *G. africana* extract is the KB05 extract, wherein the KB05 extract is in amount of 20% and wherein the *G. africana* extract comprises bioflavonoids.

6. The composition as claimed in claim 1, wherein the *G. africana* extract comprises bioflavonoids, and wherein the amount of the bioflavonoids is between 0.2 to 5.0% by weight.

7. The composition of claim 1, wherein the viscosity of the composition can be adjusted by adding a polymeric gelling agent.

8. The composition as claimed in claim 1, further comprising the following ingredients at the following concentrations:

|  | % w/w |
|---|---|
| Deionised water | 40.00 |
| Whole milk | 13.30 |
| Sodium cocoyl glutamate | 10.00 |
| Sodium N lauroylsarcosinate | 10.00 |
| Sodium laurelglucosides hydroxypropyl sulphonate | 10.00 |
| D panthenol | 0.5 |
| Betain | 0.5 |
| Propylene glycol | 4.0 |
| Cocamidopropyl hydroxysultaine | 5.0 |
| Propylene glycol + KBO5 | 5.0 |
| Phenethyl alcohol | 0.5 |
| Citric acid | ±0.2 (to pH 6.5) |
| Xanthan gum | 1.0 |
| Total | 100.0 |

9. The composition as claimed in claim 1, further comprising cocamidopropyl hydroxysultaine.

10. The composition of claim 1, further comprising a vitamin, wherein the vitamin is D-panthenol or vitamin B5 (panthothenic acid), wherein the vitamin is a nutrient that is easily absorbed by hair and skin, and wherein the vitamin has conditioning properties.

11. The composition as claimed in claim 1, further comprising natural betain, wherein the natural betain is a natural ingredient from sugar beet that has the ability to penetrate the skin and hair and act as a moisturiser and has the added advantage of reducing skin irritation.

12. The composition as claimed in claim 1, further comprising cosmetic grade xanthan gum, which is added to increase the viscosity of the product, and to improve foaming properties and skin feel.

13. The composition as claimed in claim 1, further comprising citric acid to adjust the pH.

14. The composition as claimed in claim 1, further comprising whole mammalian milk.

15. The composition as claimed in claim 1, further comprising the following ingredients at the following concentrations:

|  | % w/w |
|---|---|
| Deionised Water | 21.3 |
| Laurel Glucoside | 20.00 |
| Sodium laureth sulphate | 40 |
| Cocoamidopropyl betain | 10.00 |
| D panthenol | 0.5 |
| Betain | 0.5 |
| Sodium chloride | 5.0 |
| Propylene glycol + KBO5 | 2 |
| Phenethyl alcohol | 0.5 |
| Citric acid | ±0.2 (to pH 6.5) |
| Total | 100.0 |

* * * * *